United States Patent [19]

Breyer et al.

[11] Patent Number: 5,271,408
[45] Date of Patent: Dec. 21, 1993

[54] HYDRODYNAMIC SYSTEM FOR BLOOD FLOW MEASUREMENT

[75] Inventors: Branko Breyer; Božidar Ferek-Petrić, both of Zagreb, Croatia

[73] Assignee: Siemens Elema AB, Sweden

[21] Appl. No.: 855,658

[22] Filed: Mar. 23, 1992

[30] Foreign Application Priority Data

Mar. 25, 1991 [YU] Yugoslavia ............................ 532/91

[51] Int. Cl.$^5$ .............................................. A61B 5/02
[52] U.S. Cl. ................................... 128/673; 128/692; 73/861.71
[58] Field of Search ............... 128/691, 692, 673, 632, 128/635, 637; 73/861.85, 861.71

[56] References Cited

U.S. PATENT DOCUMENTS

| | | |
|---|---|---|
| 4,237,729 | 12/1980 | McLeod et al. |
| 4,691,709 | 9/1987 | Cohen .......................... 128/692 |
| 4,697,595 | 10/1987 | Breyer et al. |
| 4,706,681 | 11/1987 | Breyer et al. |
| 4,757,821 | 7/1988 | Snyder . |
| 4,771,787 | 9/1988 | Wurster et al. |
| 4,783,994 | 11/1988 | Ashby, Jr. ...................... 73/861.65 |
| 4,790,323 | 12/1988 | Leavitt et al. |
| 5,069,679 | 12/1991 | Taheri ............................ 128/692 |
| 5,099,686 | 3/1992 | Köhler ........................... 73/861.65 |

FOREIGN PATENT DOCUMENTS

0474957 3/1992 European Pat. Off. .

OTHER PUBLICATIONS

"Possibilities of Ultrasound Catheters," Breyer et al. Int. J. Card. Imag., vol. 6 (1991) pp. 277–284.
"Properties of Ultrasonically Marked Leads," Breyer et al. PACE, vol. 12, Aug. 1989, pp. 1369–1380.

Primary Examiner—Lee S. Cohen
Assistant Examiner—Robert L. Nasser, Jr.
Attorney, Agent, or Firm—Hill, Steadman & Simpson

[57] ABSTRACT

A device for measuring blood flow in the vicinity of a catheter implanted within the vascular vessel or the heart uses hydrodynamic principles. The device has two transducers mounted at the exterior surface of the catheter spaced from each other. One of the transducers has a protrusion in the form of a hydrofoil profile, and the other transducer presents a substantially flat surface at the exterior of the catheter. The transducer having the hydrofoil profile generates a signal due to the quasi-static pressure acting on the transducer as well as due to the drag force acting on the transducer caused by the blood flow. The other transducer generates a signal solely due to the quasi-static pressure. The transducers can either be connected with opposite polarity, or their respective signals can be subtracted in a differential amplifier, so that a signal proportional to the axial flow velocity is obtained.

7 Claims, 5 Drawing Sheets

HYDRODYNAMIC SYSTEM FOR BLOOD FLOW MEASUREMENT

BACKGROUND OF THE INVENTION

1. Field of the Invention

The present invention is related to medical technology for blood flow measurement, and in particular to a blood flow measurement device suitable for controlling the operation of a cardiac pacemaker.

2. Background and Prior Art

Measurement of blood flow velocity can be undertaken transcutaneously (through the skin) or intraluminally (directly within the flow). The present invention relates to techniques for intraluminal flow measurements.

Intraluminal flow measurement is needed in all invasive cardiovascular procedures, e.g., catheterization, pacemaker applications and cardiovascular surgery.

Currently such measurements are undertaken using Doppler methods as well as by thermodilution techniques. Measurements using the Doppler effect function by means of transmission of ultrasound energy in the form of a pulse or a continuous wave into the blood stream, and detection of the Doppler frequency shift of the received, reflected waves. Techniques for undertaking measurements of this type are described in Yugoslavian pending patent application P1852/89, in U.S. Pat. Nos. 4,790,323, 4,771,787, 4,706,681, and 4,697,595, as well as in the paper "Properties of Ultrasound Catheters," B. Breyer and B. Ferik-Petric, in the book "Intracavitary Ultrasound" published by Kluwer, Inc., 1991, edited by N. Bom and N. Roelant.

Using these known techniques, with appropriate frequency filtering, data is obtained regarding the flow in the volume within the field of view of the Doppler system, i.e., in the proximity of a catheter. The advantage of such ultrasound techniques is that it is a direct measurement of the flow, but disadvantages are the relatively high power consumption and sophisticated electronics which are necessary in such Doppler systems.

Another method for bulk flow estimation is that of thermodilution, in which thermometers mounted on a catheter measure the rate of cooling of the blood stream after the injection into the stream of a liquid of a different temperature. The advantage of this method is its simplicity, but disadvantages are the relatively poor accuracy and the necessity of undertaking time averaging of the measurement. This method has been known in medical technology for over 20 years, and is the result of the state of electronics at the time of its development.

SUMMARY OF THE INVENTION

It is an object of the present invention to provide a new method for intraluminal blood flow velocity measurement which combines the advantages of the thermodilution method and the Doppler method, but avoids the disadvantages of those methods.

More specifically, it is an object of the present invention to provide such a method for intraluminal blood flow velocity method which has low power consumption, as in the thermodilution method, but has frequency handling capability comparable to the Doppler method.

The method and apparatus disclosed herein are based on the physical principle of the fluid energy continuance described with Bernoulli equations. The method disclosed herein is mathematically equivalent to measurement by means of the Pitot method and Venturi tube, but the apparatus disclosed herein is technologically different.

The apparatus disclosed herein is for the purpose of undertaking measurement of the blood flow in the vicinity of a catheter implanted in a blood vessel or the heart. The flow must be measured without introducing additional disturbances to the flow, and the measurement must be undertaken with a frequency spectrum which covers the relevant frequencies present in the flow. The power consumption must be low, and therefore the system must be passive, i.e., it should not transmit any energy into the body. The system must be small enough to be constructed on a catheter of 2.7 mm diameter or larger, and must be sufficiently rugged so as not to be damaged by implantation procedures using a standard venous introducer. The system proportions and dimensions should not degrade the catheter flexibility, and therefore the rugged section should not be longer than 1.5 cm. The system must be insensitive to changes in atmospheric or body pressure. The system cannot cause erythrocyte trauma, or thrombocyte reaction, nor can it cause cholesterol sedimentation.

The objects are achieved in accordance with the principles of the present invention in a device for blood flow measurement in the vicinity of a catheter implanted within a vascular vessel or the heart which measures the flow velocity using the principles of hydrodynamics, i.e., events described by means of the Bernoulli equations. The device has two transducers mounted at the surface of a catheter, spaced from each other. One of the transducers has a protrusion from the catheter surface, which may be glued or otherwise fixed to the surface, in the shape of a hydrofoil profile (i.e., an underwater wing). The other transducer is generally in the form of a band surrounding the transducer, and presents a generally flat exterior surface to the blood flow. The transducer having the hydrofoil profile generates an electrical signal due to the surround quasi-static pressure acting on the transducer, as well as due to the drag force acting on the transducer caused by the blood flow. The other transducer generates an electrical signal solely due to the quasi-static pressure. The transducers can either be connected with opposite polarity, or their respective signals can be subtracted in a differential amplifier, so that a difference signal is obtained which represents the axial flow velocity. The system enables a real time flow velocity measurement by means of simple electronic circuits and with low energy consumption in comparison to known methods. Because the system can be easily implemented on a catheter, it is suited for implantation as part of a cardiac pacemaker system, with the flow velocity measurement obtained by the system being used, as needed, to control the operation of the pacemaker.

DESCRIPTION OF THE PREFERRED EMBODIMENTS

The hydrodynamic system for blood flow measurement disclosed herein is based on the solution of the hydrodynamic problem using the Bernoulli equation. Two sets of piezoelectric transducers are mounted on an intraluminal device, such as a catheter, at a small distance from each other, e.g. 1 cm. One transducer set, referred to as the static set or static transducer, is mounted on the catheter in a manner so as not to disturb the flow and stream around the catheter. It is covered with a flexible insulating and waterproof membrane having a thickness of less than 0.1 mm. This transducer set is therefore exposed to the pressure of the surrounding liquid.

A further transducer set, referred to as the dynamic set or the dynamic transducer, is also mounted on the exterior of the catheter, in a manner similar to the static set, but has an outer protrusion consisting of plastic material having a cross section in the shape of a laminar flow hydrofoil or airfoil (e.g. NACA 4512), which increases the flow velocity in the immediate vicinity of this transducer set, thereby inducing a lift force as predicted by the Bernoulli equation.

Figure 3:
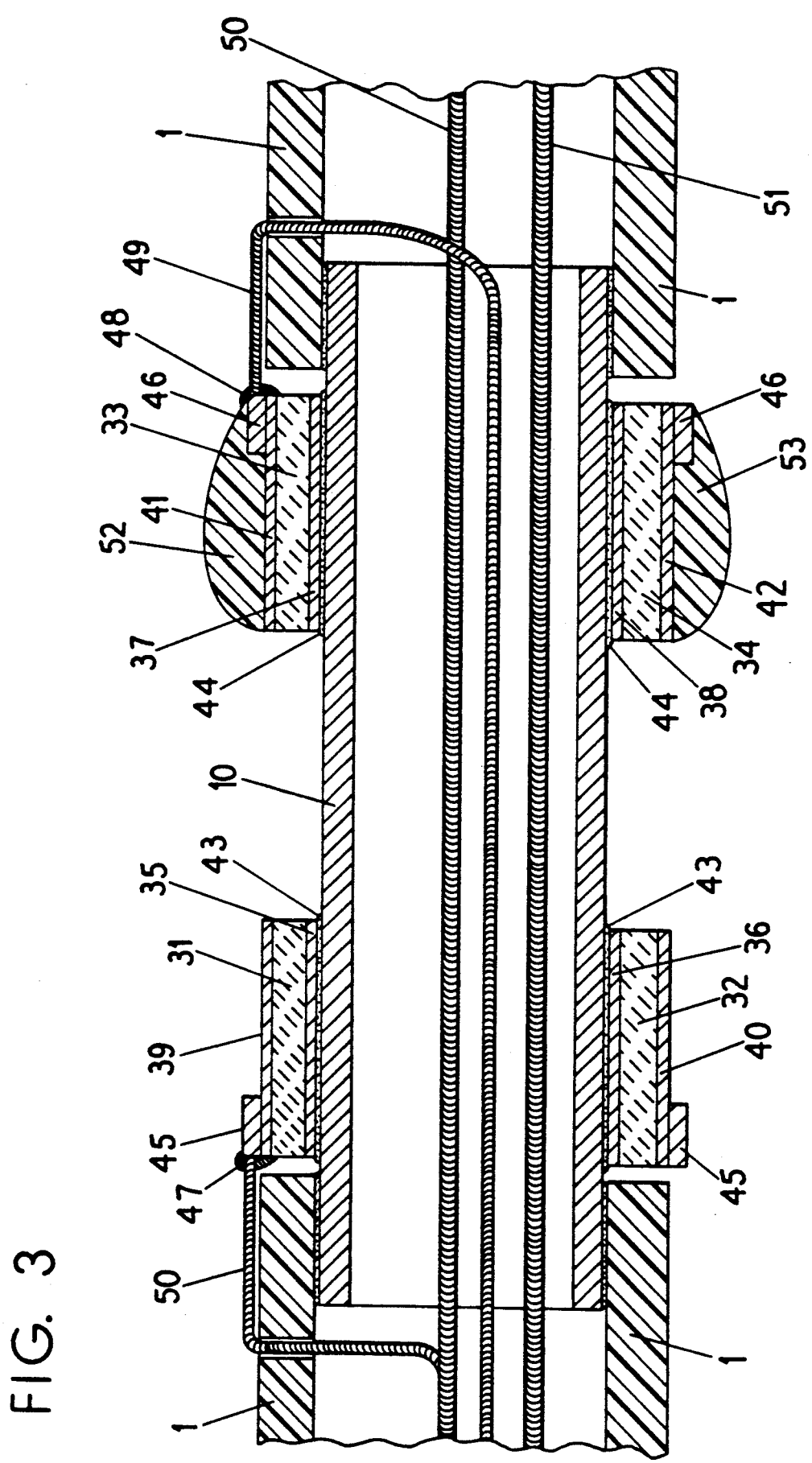
FIG. 3 is a longitudinal cross section of the portion of the catheter shown in FIG. 2, in a first embodiment.
Figure 4:
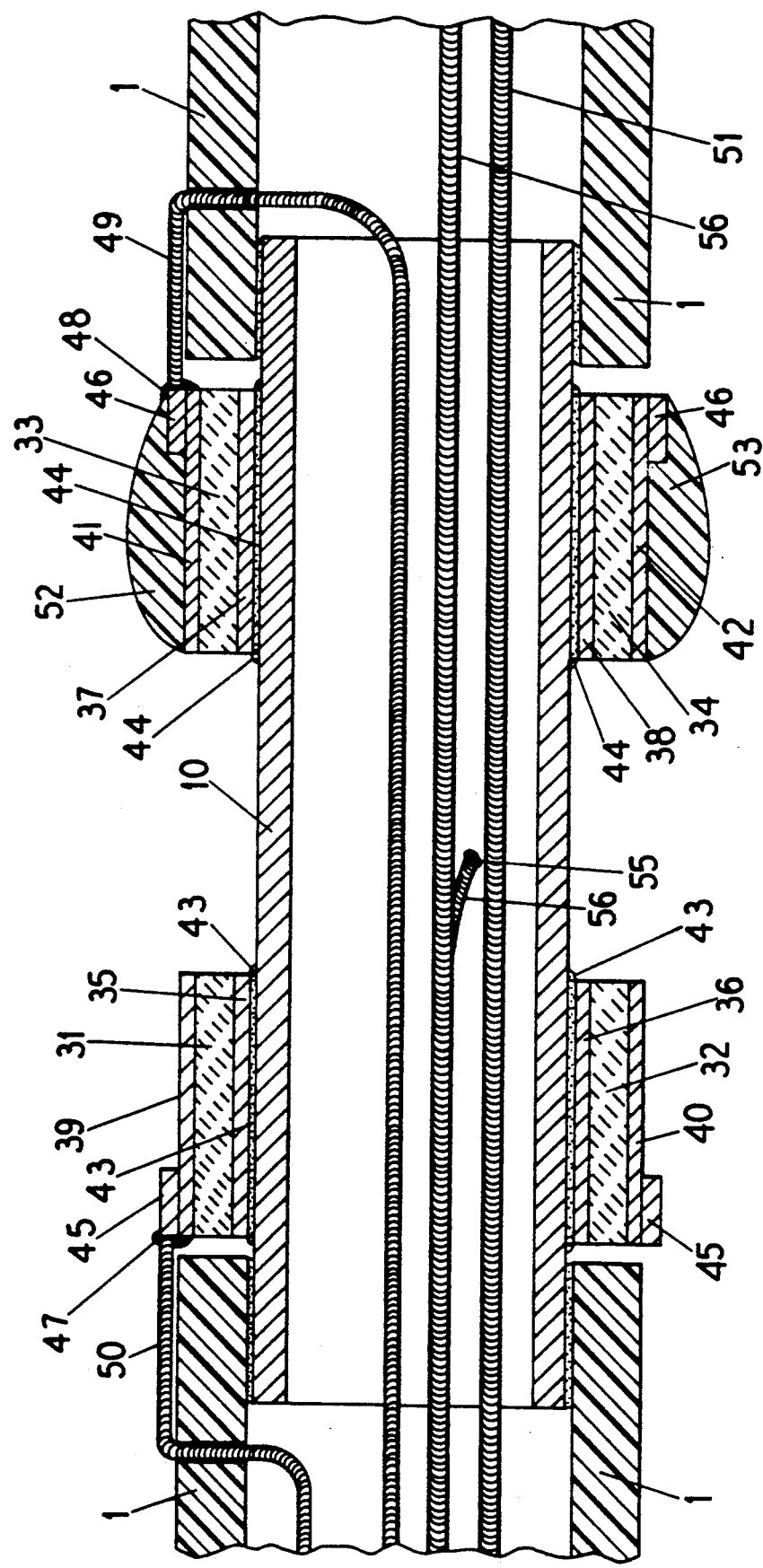
FIG. 4 is a longitudinal cross section of the portion of the catheter shown in FIG. 2 in a second embodiment.

This lift force and the associated induced drag force are proportional to the square of the fluid velocity. The sensitivity of the dynamic transducer set to hydrostatic pressure is equal to that of the static transducer set. In order to cancel the influence of the static pressure, which is much larger than the hydrofoil lift, the transducer sets can be connected with opposite polarities, as shown in FIG. 3, or can be connected independently as shown in FIG. 4, in which case the respective transducer signals are subtracted in a differential amplifier.

Figures 1, 2:
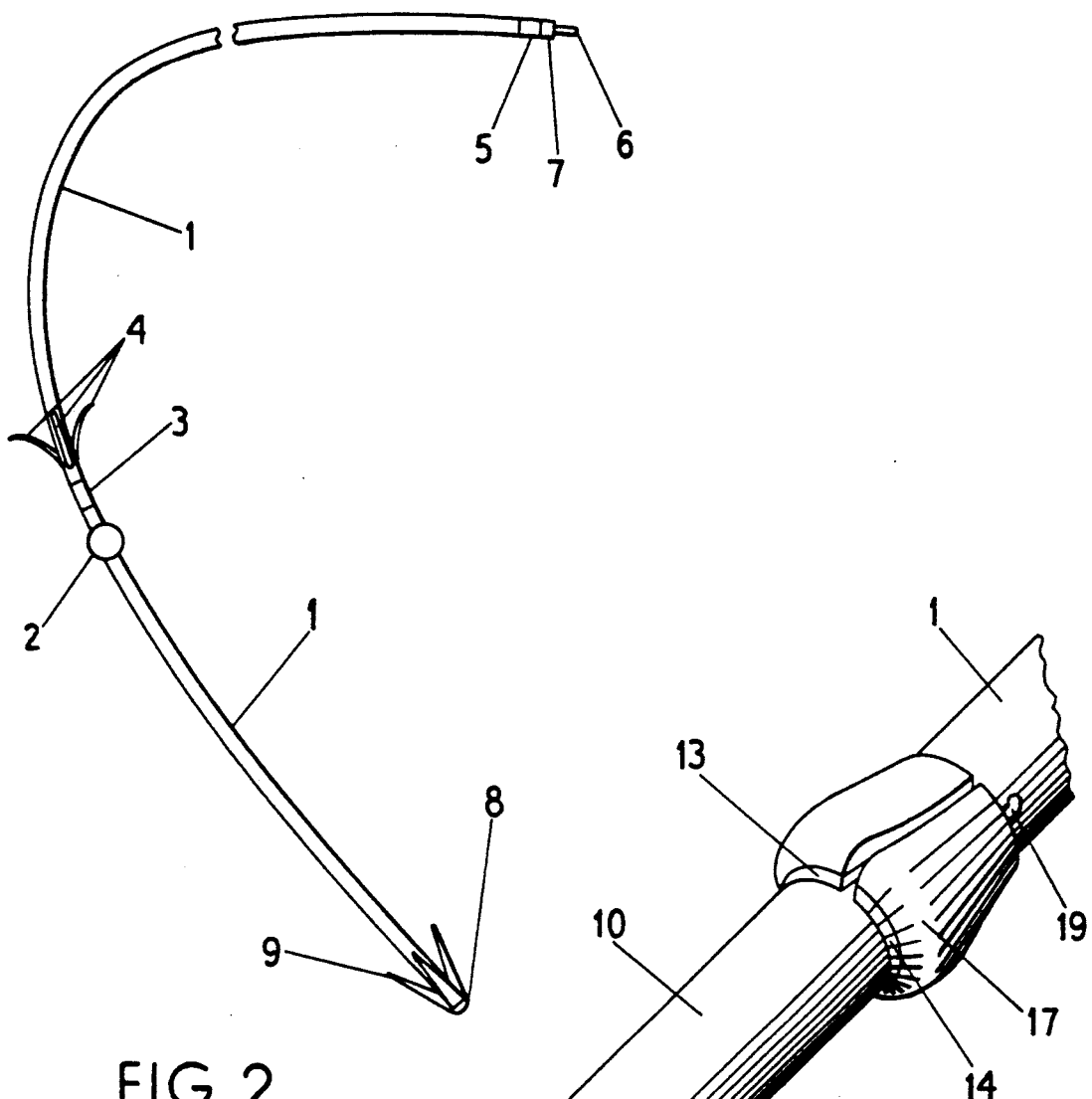
FIG. 1 is a perspective view of a cardiac pacemaker lead embodying a hydrodynamic system for blood flow measurement constructed in accordance with the principles of the present invention.
FIG. 2 is an enlarged, detailed perspective view of the portion of the catheter of FIG. 1 embodying the hydrodynamic system for blood flow measurement constructed in accordance with the principles of the present invention.

Mounting of the measurement system on a standard catheter is shown in FIG. 1, with further details of the measurement system in different embodiments being shown in FIGS. 2 through 6.

As shown in FIG. 1, two sets 2 and 3 of piezoelectric transducers are mounted on a catheter 1. The portion of the catheter 1 on which the transducer sets 2 and 3 are mounted is reinforced with metal or a reinforcing plastic tube (formed by conductive plastic). As shown in greater detail in other figures, the transducer set 2 has a hydrofoil profile mounted thereon and is thus referred to as the dynamic transducer set. The transducer set 3 is the static transducer set. The transducers are connected to electrical connector assembly 5, 6 and 7 via internal electrical conductors (not shown), shown in greater detail in other figures. The conductors (not shown) carry the measurement electrical signals as well as electrical stimulation signals, which are delivered at an exposed, electrically conductive electrode tip 8, being electrically connected to the pin 6 of connector assembly. The electrode tip 8 is anchored in contact with the endocardium by fins 9 or some other anchoring means. Centralizing means enables positioning of transducer sets apart from the wall of a blood vessel, when system is used in a great cardiac vessel.

A detailed, enlarged showing of the measurement transducer assembly, in a first embodiment, is shown in FIG. 2. The two transducer sets are mounted on a reinforcing tube 10 made of plastic or metal and having a size which fits into the catheter 1. Each transducer set consists of a number of piezoelectric cylindrical segments which are conductively glued or soldered to the reinforcing tube 10, so that the device is axially symmetrical. In the embodiment shown in FIG. 2, each transducer set consists of two such segments, the static set being formed by piezoelectric segments 11 and 12 and the dynamic set being formed by piezoelectric segments 13 and 14. All properties for any one of the segments of the transducers are the same for the other segments. On the respective outer and inner sides of the transducers are thin, fired-on electrodes. The piezoelectric segment 11 has an exterior electrode 15 and the piezoelectric segment 12 has an exterior electrode 16, the respective inner electrodes not being visible in FIG. 2. The static transducer set has a flat exterior profile, and is covered only with an insulating membrane (not shown).

The dynamic transducer set also has inner and outer electrodes, however, the outer electrodes for that set cannot be seen in FIG. 2 because the piezoelectric segments 13 and 14 are covered by a hydrofoil element 17. The hydrofoil element 17 is glued to the exterior of the piezoelectric segments 13 and 14. Both sets of transducers will thus be acted upon by quasi-static pressures which are respectively substantially the same, however, the dynamic transducer set will additionally be subjected to drag forces caused by the hydrofoil element 17. The difference between the total electrical signal output of the transducer sets will therefore correspond only to the drag forces, which in turn correspond to the flow velocity. For this purpose, electrical connections are provided, which in the embodiment of FIG. 2 are formed by conductors 18 and 19 which conduct the output signals from the piezoelectric segments into the catheter body where they are connected to respective internal conductors 20 and 21. The electrical connection to the respective exterior electrodes of the transducer segments are in the embodiment of FIG. 2 achieved by elastic conductive rings 22, the ring 22 for the static transducer set being visible in FIG. 2, with the other ring for the dynamic transducer set being covered by the hydrofoil element 17. The electrical connection to the inner transducer electrodes is achieved by the conductive reinforcing tube 10.

A longitudinal section of the catheter portion of FIG. 2 is shown in FIG. 3. This is a so-called self-compensating measurement system embodiment. The insulating covering of the catheter (pacing lead) 1 holds the reinforcing tube 10. Identical piezoelectric transducer segments 31, 32, 33 and 34 are shown, the segments 31 and 32 forming the static set and the segments 33 and 34 forming the dynamic set. These segments have respective fired-on inner sheath electrodes 35, 36, 37 and 38, and respective outer fired-on electrodes 39, 40, 41 and 42. There may be three or four transducer segments per transducer set, which cannot be seen in a longitudinal section, but will be arranged with axial symmetry on the device. The respective inner sheath electrodes 35 and 36 are conductively glued or soldered at 43 and 44 to the conductive reinforcing tube 10. The outer electrodes of all of the piezoelectric segments in a set are electrically connected with elastic conductors, i.e., an elastic conductive ring 45 for the static set containing segments 31 and 32 and an elastic ring 46 for the dynamic transducer set containing segments 33 and 34.

The elastic conductive rings 45 and 46 are connected by gluing or soldering at 47 and 48 to respective conductors 49 and 50, which conduct the output signals from the piezoelectric segments to one or more remotely located electronic circuits. One or more further conductors, such as conductor 51, may be present as well inside the catheter 1 for other purposes, such as supplying stimulation pulses for pacing.

The dynamic set of transducers has hydrofoil profiles or protrusions 52 and 53, such as an NACA 4512 or Goettingen laminar profile. The profiles 52 and 53 cause a difference in the total output signals of the two transducer sets, i.e., the difference between the signals conducted by conductors 49 and 50, which is proportional to the square of the axial flow velocity.

Figure 7A:
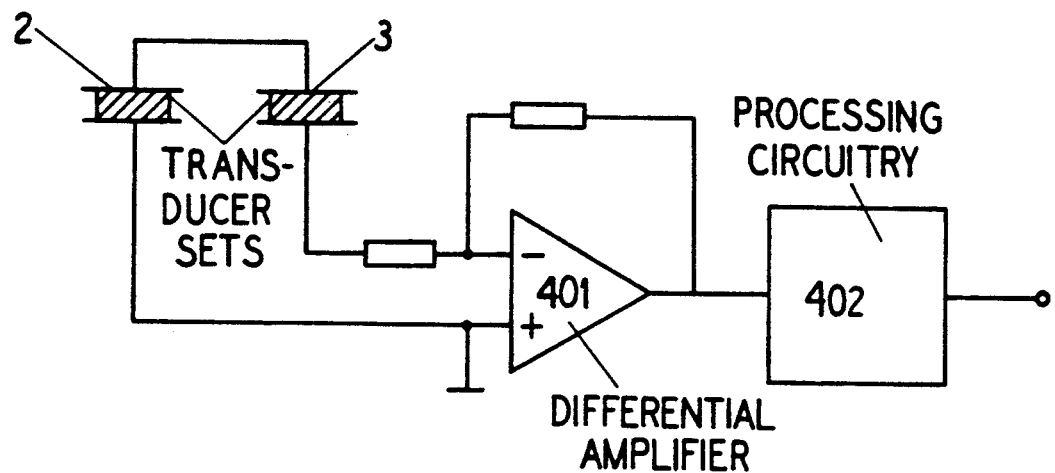
FIG. 7A is a schematic diagram of a circuit for obtaining a signal corresponding to blood flow from the two transducers in accordance with the principles of the present invention, in a first embodiment.
Figure 7B:
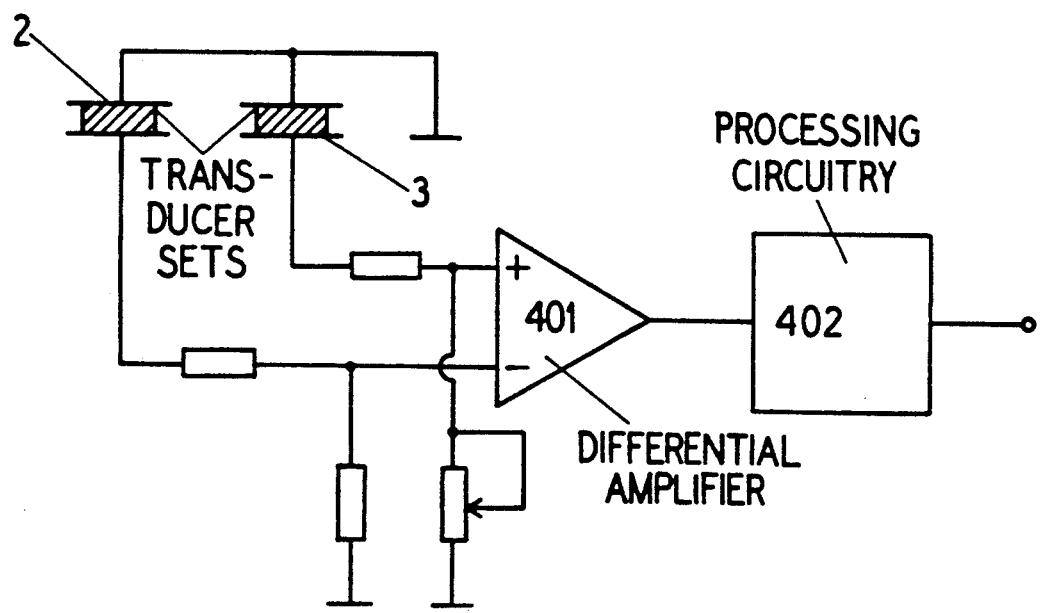
FIG. 7B is a schematic diagram of a circuit for obtaining a signal corresponding to blood flow from the two transducers in accordance with the principles of the present invention, in a second embodiment.

A longitudinal cross section of a further embodiment, which is not self-compensating is shown in FIG. 4. This embodiment differs from the embodiment in FIG. 3 primarily in the different manner of electrical connections. Structural components which are the same as in the embodiment of FIG. 3 are provided with the same reference numerals in FIG. 4. In the embodiment of FIG. 4, a conductor 56 is soldered or conductively glued at 55 to the reinforcing tube 10. This results in three conductors 49, 50 and 56 which conduct the transducer signals to the remote electronics. The electrical signals in this embodiment are thus independent, and can be combined as desired in the remote electronic circuits, such as are shown in FIGS. 7A and 7B.

Figure 5:
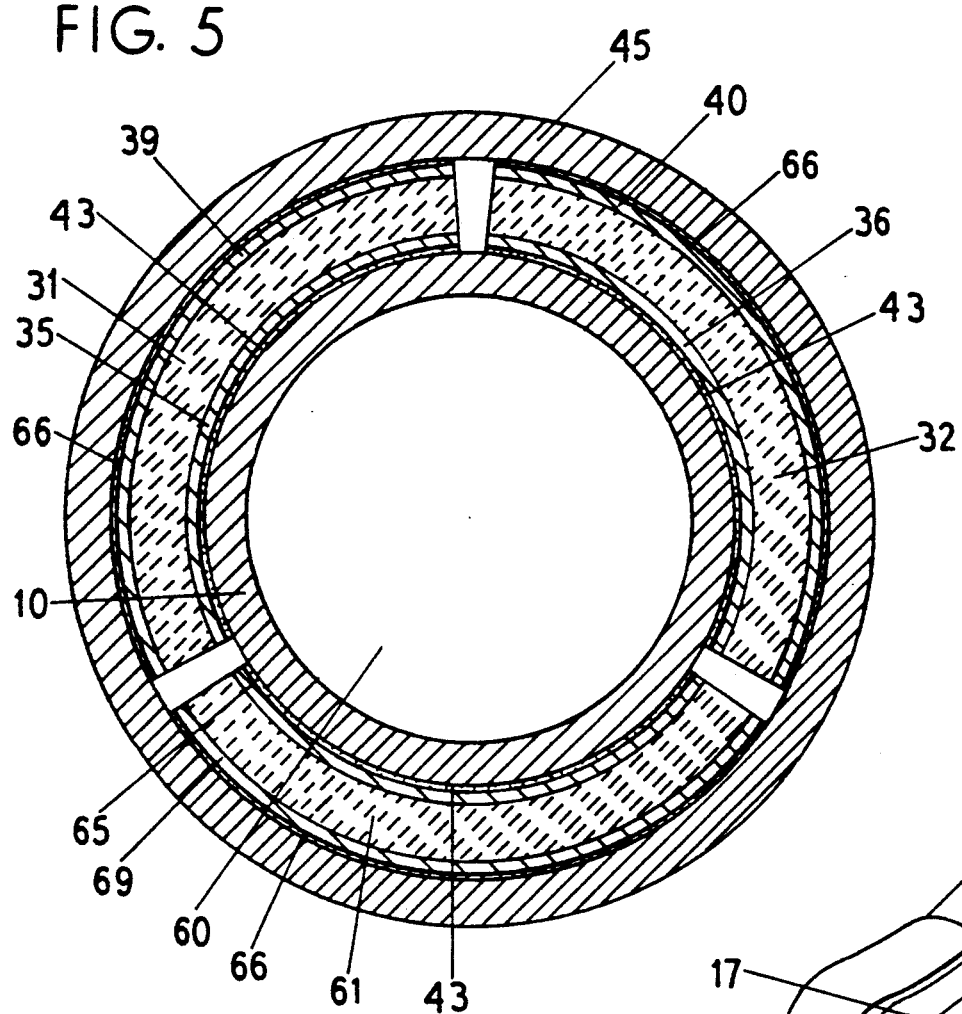
FIG. 5 is a transverse cross section taken along line V—V of FIG. 3.

Further details of the structure are shown in FIG. 5 which is a transverse cross section through the static transducer set in the embodiment of FIG. 3. The lumen of the catheter or pacing lead 1 can accommodate all of the necessary conductors, which are omitted for clarity in FIG. 5. In the cross-sectional view of FIG. 5, a further transducer segment 61 can be seen, which was not visible in the longitudinal section of FIG. 3. The piezoelectric transducer segments 31, 32 and 61 are independently mechanically glued at 43 to the reinforcing tubing 10. Their respective inner electrodes 35, 36 and 65 are electrically connected together by the conducting reinforcing tube 10. Their external electrodes 39, 40 and 69 are electrically connected together by the elastic conductive ring 45. The conductive ring 45 may be formed, for example, by metallized plastic foil less than 10 mm thick, however, in FIG. 5 the ring 45 is shown with an enlarged thickness for clarity.

The hydrofoil projection glued to the dynamic transducer set is segmented in the same manner as the transducer segments. In all embodiments, the number of segments is two or more.

Figure 6:
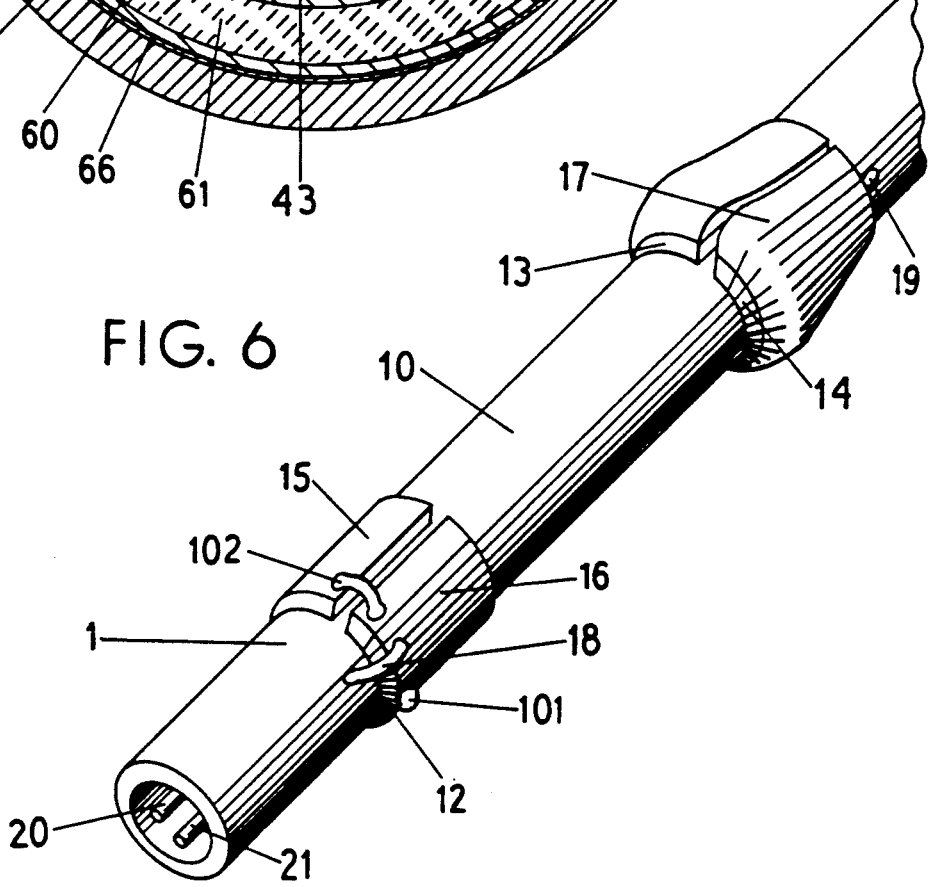
FIG. 6 is an enlarged detailed view of the portion of the catheter shown in FIG. 1 embodying the hydrodynamic system for blood flow measurement constructed in accordance with the principles of the present invention, in a further embodiment.

A further embodiment of the electrical connection of the transducer segments is shown in FIG. 6, which makes use of interconnecting bridges 101 and 102 instead of the conducting ring. The bridges 101 and 102 may consist of braided wire or strip. Because of the perspective view, only two such bridges can be seen in FIG. 6, however, it will be understood that all of the piezoelectric transducer segments are connected by means of such bridges.

Two embodiments of the electronics portion of the measurement system are shown in FIGS. 7A and 7B. In both embodiments, signals generated by the transducer sets 2 and 3 are supplied to the respective inputs of a differential amplifier 401. The circuit in FIG. 7A is for use with a conductor arrangement for the transducer sets as shown in the embodiment of FIG. 3, whereas the circuit shown in FIG. 7B is for use with a conductor arrangement as shown in the embodiment of FIG. 4. In the embodiment of FIG. 7A, the static signals from the two transducer sets 2 and 3 are cancelled within the catheter, by virtue of connection with opposite polarity to the respective transducers, so that only the difference between those signal is supplied to the amplifier 401. In the embodiment of FIG. 7B, the static component of the respective signals from the transducer sets 2 and 3 is subtracted within the amplifier 401. The amplifier 401 is a stable operational amplifier of the type well-known in the electronics art. The output signal of the amplifier 401 is supplied to further signal processing circuitry, generally shown at 402, which may include filtering and analog-to-digital conversion, in order to extract the required information for a particular use by any number of known techniques.

Although modifications and changes may be suggested by those skilled in the art, it is the intention of the inventors to embody within the patent warranted hereon all changes and modifications as reasonably and properly come within the scope of their contribution to the art.

We claim as our invention:

1. A hydrodynamic system for blood flow velocity measurement comprising:

a catheter adapted for long-term in vivo implantation in a blood flow;

first and second passive transducer means carried on said catheter at a side of said catheter and spaced from each other and interactable with said blood flow for respectively generating signal components corresponding to static pressure of said blood flow at each passive transducer means;

hydrofoil profile means mounted on only one of said passive transducer means and interactable with said blood flow for causing said one of said passive transducer means to generate a further signal component proportional to the velocity of said blood; and electrically conductive means connected to said first and second passive transducer means for conducting said signal components and said further signal component through said catheter.

2. A hydrodynamic system as claimed in claim 1 wherein each of said passive transducer means consists of a plurality of piezoelectric transducer segments.

3. A hydrodynamic system as claimed in claim 2 wherein said segments are symmetrically arranged around said catheter.

4. A hydrodynamic system as claimed in claim 1 wherein said hydrofoil profile means is mounted at an exterior of said one of said passive transducer means and projects beyond an exterior surface of said catheter.

5. A hydrodynamic system as claimed in claim 1 wherein each of said first and second passive transducer means has a polarity, and wherein said electrically conductive means is connected to said first and second passive transducer means with opposite polarity.

6. A hydrodynamic system as claimed in claim 1 further comprising means connected to said electrically conductive means for forming a difference between said signal component and said further signal component from said one of said passive transducer means and the signal component from the other of said transducer means.

7. A hydrodynamic system as claimed in claim 1 further comprising reinforcing means attached to said catheter to which said first and second passive transducer means are mounted.

* * * * *